(12) United States Patent
Mamchur

(10) Patent No.: US 7,858,607 B2
(45) Date of Patent: Dec. 28, 2010

(54) SYSTEM FOR USE BY COMPOUNDING PHARMACISTS TO PRODUCE HORMONE REPLACEMENT MEDICINE CUSTOMIZED FOR EACH CONSUMER

(76) Inventor: Stephen A. Mamchur, 2345 10th Avenue West, Prince Albert, Saskatchewan (CA) S6V-7Y6

( * ) Notice: Subject to any disclaimer, the term of this patent is extended or adjusted under 35 U.S.C. 154(b) by 1490 days.

(21) Appl. No.: 10/668,075

(22) Filed: Sep. 22, 2003

(65) Prior Publication Data

US 2004/0180866 A1    Sep. 16, 2004

Related U.S. Application Data

(60) Provisional application No. 60/454,915, filed on Mar. 14, 2003.

(51) Int. Cl.
    *A61K 31/56*    (2006.01)
    *A61K 31/045*   (2006.01)
    *A61K 31/08*    (2006.01)
    *A61K 47/00*    (2006.01)

(52) U.S. Cl. .......... 514/177; 514/169; 514/170; 514/171; 514/178; 514/179; 514/182; 514/723; 514/738; 514/772; 514/841; 514/843; 514/874; 514/899; 514/947; 424/198.1

(58) Field of Classification Search ............ 514/177
    See application file for complete search history.

(56) References Cited

U.S. PATENT DOCUMENTS

| | | | | |
|---|---|---|---|---|
| 2,856,329 A | * | 10/1958 | Taylor et al. ........... | 514/171 |
| 3,828,106 A | * | 8/1974 | Rudel ..................... | 514/170 |
| 4,076,811 A | * | 2/1978 | Lachnit-Fixson et al. ... | 514/170 |
| 5,665,377 A | * | 9/1997 | Gonella ................. | 424/448 |
| 5,709,878 A | * | 1/1998 | Rosenbaum et al. ..... | 424/449 |
| 5,736,161 A | | 4/1998 | Garces | |
| 5,891,462 A | | 4/1999 | Carrara | |
| 6,248,363 B1 | * | 6/2001 | Patel et al. ............ | 424/497 |
| 6,303,132 B1 | * | 10/2001 | Nelson .................. | 424/400 |
| 6,541,001 B1 | * | 4/2003 | Gallili et al. .......... | 424/184.1 |
| 6,708,822 B1 | * | 3/2004 | Muni .................... | 206/438 |
| 6,967,194 B1 | | 11/2005 | Matsuo et al. | |
| 2001/0023261 A1 | | 9/2001 | Ryoo | |
| 2002/0173669 A1 | * | 11/2002 | Schultz et al. ......... | 552/515 |
| 2003/0077297 A1 | * | 4/2003 | Chen et al. ............. | 424/400 |
| 2003/0109512 A1 | | 6/2003 | Kucharchuk | |
| 2003/0165568 A1 | | 9/2003 | Colombo | |
| 2005/0129779 A1 | * | 6/2005 | Dal Farra et al. ....... | 424/526 |
| 2007/0190120 A1 | * | 8/2007 | Rosario-Jansen et al. ... | 424/443 |

FOREIGN PATENT DOCUMENTS

| | | |
|---|---|---|
| EP | 0811381 A | 12/1997 |
| GB | 821989 | 10/1959 |
| WO | WO 90/04397 | 5/1990 |
| WO | WO 90/11064 A1 * | 10/1990 |
| WO | WO 97/24148 A1 * | 7/1997 |
| WO | WO 02/11768 | 2/2002 |
| WO | WO 02/11768 A1 * | 2/2002 |
| WO | WO 03/066019 | 8/2003 |
| WO | WO 03/068186 | 8/2003 |
| WO | WO 03/105775 | 12/2003 |
| WO | WO 2004/012653 | 12/2004 |
| WO | WO 2005/027911 | 3/2005 |

* cited by examiner

*Primary Examiner*—John Pak
*Assistant Examiner*—Nathan W Schlientz
(74) *Attorney, Agent, or Firm*—Hodes, Pessin & Katz, P.A

(57) ABSTRACT

The invention concerns a concentrated hormone pharmaceutical composition having from about 0.6 to about 80% of at least one hormone; from about 20 to about 90.4% of at least one solvent, and optionally a pharmaceutically acceptable carrier. The concentrated hormone pharmaceutical composition according to this invention provides a concentrated pharmaceutical composition that is easy to use and saves time and money to the pharmacies dealing with BHRT pharmaceutical products.

29 Claims, No Drawings

SYSTEM FOR USE BY COMPOUNDING PHARMACISTS TO PRODUCE HORMONE REPLACEMENT MEDICINE CUSTOMIZED FOR EACH CONSUMER

REFERENCE TO RELATED APPLICATIONS

This application is a non-provisional of Provisional Application No. 60/454,915 filed Mar. 14, 2003.

BACKGROUND OF THE INVENTION

1. Field of the invention

This invention relates to a concentrated hormone pharmaceutical composition to be used in the production of hormone replacement therapies.

2. Description of the related art

Natural Hormone Replacement Therapy has been around for more than twenty years. The term "natural" comes from the fact that the hormones (estrogens such as estradiol, estrone, and estriol, testosterone, DHEA, pregnenolone and progesterone) come from natural sources. However, more importantly, the term means that the hormones have the exact same molecular structure as those produced by the body itself, thus the body recognizes the hormones as being "natural", because they are "bio-identical", therefore, the shift to a more appropriate name, Bio-identical Hormone Replacement Therapy (BHRT).

Some of the benefits of BHRT include: fewer side effects compared with traditional HRT; protection against heart disease, reduced risk of breast cancer, and improved lipid profile.

Bio-identical Hormone Replacement Therapy products are compounded by a compounding pharmacist, which offers you and your physician a choice for individualized hormone replacement. Generally the BHRT pharmaceutical compositions are sold in the form of ointments, creams, gels, pastes, capsules, troches, lozenges, lollipops, tablet triturates, sublingual tablets, and tablets.

A BHRT ointment, cream, gel, or paste may include, but is not limited to, the active hormone or hormones, a suitable solvent or solvents, including, but not limited to, ethoxy diglycol, propylene glycol, alcohol, or glycerin and any suitable ointment, cream, or gel base which allows for transdermal absorption of bio-identical hormones.

Producing BHRT pharmaceutical compositions is a very lucrative business for compounding pharmacies. However, the process of producing the BHRT pharmaceutical compositions is an extremely time-consuming process and has many risks and subsequent costs associated with the compounding of BHRT pharmaceutical compositions.

One of the main problems with compounding BHRT pharmaceutical compositions is the substantial risk of employee contamination (inhalation or transdermal absorption of the hormones) with the hormones. The hormones used for producing the BHRT pharmaceutical compositions are naturally found in the body in physiological levels. Thus, when a human is chronically exposed to higher than normal levels of these hormones, they are at risk of developing serious adverse medical effects, including, but not limited to, an unnatural increased response by each system of the body which is affected by each individual hormone, as well as an increased risk of developing numerous varieties of cancer.

In addition, producing these BHRT pharmaceutical compositions requires great skill and knowledge. It also requires expensive equipment such as accurate electronic scales, electronic mortars and pestles (EMP), and ointment mills.

In order to diminish these risks, the compounding pharmacies have developed an expensive and time-consuming method to reduce employee exposure to these hormones. These measures include, but are not limited to, the use of a custom built clean room, high velocity air flow units fitted with high emission particulate air (HEPA) filters, custom built ventilation systems, protective suits, protective eyewear, protective gloves, and protective HEPA filter masks.

The production of BHRT pharmaceutical compositions is by itself a time-consuming process. Each ointment, cream, gel, or paste must be specifically engineered for each patient based on his or her distinct hormone profile, thus the use of bulk compounding is precluded, because each medication is produced custom fit for each patient.

Furthermore, bulk compounding or manufacturing of hormone products is illegal in most states without a proper license.

In order to produce these BHRT pharmaceutical compositions safely and accurately, compounding pharmacies need to invest a great deal of time and money into these safety measures. The pharmacies would also need to employ a specially trained staff; all these measures decrease productivity substantially.

These measures are not only expensive, but also create an unpleasant work environment. This is due to the fact that the employee is covered from head to toe in restrictive, uncomfortable protective gear. They are also working in a room, which is noisy because of the high velocity ventilation systems, which are in constant use.

In order to work with BHRT pharmaceutical compositions, an employee must:

Be trained in the art of compounding BHRT ointments, creams, gels, and pastes.

Ensure they are wearing all the necessary protective gear.

Locate all of the ingredients.

Weigh all of the ingredients in the appropriate environment, a clean room with proper ventilation and filtration systems, to prevent exposure to harmful chemicals.

Combine the ingredients using the EMP to ensure thorough mixing. If the mixture is not thoroughly mixed, then it will not contain a uniform concentration of the drug throughout.

Run the mixture through an ointment mill to decrease the particle size of the drug. This will increase absorbability, as smaller drug particles will more readily penetrate the dermis. This process also ensures a non-gritty, pharmaceutically elegant, and cosmetically pleasing final product.

The combination of the potential risks associated with producing BHRT pharmaceutical compositions, specially trained employees to compound these compositions safely and accurately, purchasing all the necessary equipment and safety measures, and the actual time required to compound each individual pharmaceutical composition result in an extremely time-consuming, hazardous, and expensive process.

The present inventor thought of the necessity of providing pharmacies with a system that is easy to use and saves time and money for those pharmacies dealing with BHRT pharmaceutical products while decreasing risk and increasing product quality.

SUMMARY OF THE INVENTION

The invention offers at least one of the following advantages:

- a system of concentrated pharmaceutical compositions that is easy to use and saves time and money to the pharmacies dealing with BHRT pharmaceutical products;
- individualized BHRT products such as ointments, creams, gels, or pastes; and
- a color-coded hormone pharmaceutical composition.

The concentrated composition of the present invention can be manufactured to contain a higher concentration of hormone (or combination of hormones) than the standard concentration of hormones prescribed by physicians, thus the pharmacist can easily measure the amount required to be incorporated into the BHRT product.

The concentrated composition of the present invention could include any concentration of any hormone or any combination of hormones in any proportion as long as the concentration is greater than the accepted physician prescribed concentrations to treat hormone deficiencies.

The present invention, also relates to a metered dispensing device including the composition of the invention to provide a means to measure and combine, quickly and accurately, quantities of hormones with appropriate ointment, cream, or gel bases by the compounding pharmacist while minimizing exposure to hazardous airborne hormone particles. Thus, airborne particles are drastically reduced because the hormones are incorporated into a liquid or semi-solid form.

The present invention relates to a concentrated hormone pharmaceutical composition comprising:
- from about 0.6 to about 80% of at least one hormone;
- from about 20 to about 90.4% of at least one solvent, and
- optionally a pharmaceutically acceptable carrier.

In the preferred embodiment, the concentrated hormone pharmaceutical composition is chosen from estradiol, estrone, estriol, testosterone, DHEA, pregnenolone, progesterone, or combination thereof.

The invention also relates to a concentrated hormone pharmaceutical composition comprising:
- from about 0.6 to about 50% of at least one hormone;
- from about 50 to about 90.4% of at least one solvent, and
- optionally a pharmaceutically acceptable carrier
- wherein the at least one hormone is chosen from estriol, estradiol, or combination thereof.

The at least one hormone is a combination of estriol and estradiol in a ratio of 5:5, 6:4, 7:3, 8:2, or 9:1.

Furthermore, the invention concerns a concentrated hormone pharmaceutical composition comprising:
- from about 0.6 to about 50% of at least one hormone;
- from about 50 to about 90.4% of at least one solvent, and
- optionally a pharmaceutically acceptable carrier
- wherein the at least one hormone is chosen from estriol, estradiol, estrone, or combination thereof.

The at least one hormone is a combination of estriol, estradiol, and estrone in a ratio of 5:4:1, 6:3:1, 7:2:1, or 8:1:1.

Furthermore, the invention concerns a concentrated hormone pharmaceutical composition comprising:
- from about 0.8 to about 80% of at least one hormone;
- from about 20 to about 90.2% of at least one solvent, and
- optionally a pharmaceutically acceptable carrier
- wherein the at least one hormone is testosterone.

In addition, the invention concerns a concentrated hormone pharmaceutical composition comprising:
- from about 8 to about 90% of at least one hormone;
- from about 10 to about 92% of at least one solvent, and
- optionally a pharmaceutically acceptable carrier
- wherein the at least one hormone is progesterone.

Furthermore, the invention concerns to a color-coded concentrated hormone pharmaceutical.

Furthermore, the invention concerns a method for producing a concentrated hormone pharmaceutical composition, the method comprising the steps of:
- measuring at least one hormone, a solvent and/or optionally a carrier by using an electronic balance in a clean room;
- combining the ingredients of step a by using an industrial scale mixer to ensure thorough mixing; and
- running the mixture of step b through a large-scale ointment mill or homogenizer to decrease the particle size of the drug, and
- optionally, heating the concentrate to facilitate the formation of a solution,
- wherein the hormone concentration is from about 0.6 to about 80%.

Furthermore, the present invention concerns a concentrated hormone pharmaceutical composition comprising:
- at least one hormone;
- optionally a powdered base;
- wherein the at least one hormone is chosen from estriol, estradiol, estrone, or combination thereof; and
- wherein the composition is in a powdered form.

Finally, the invention concerns a kit for producing a liquid or semi-solid concentrated hormone pharmaceutical composition, the kit comprising:
- at least one hormone;
- at least one solvent, and
- optionally a pharmaceutically acceptable carrier,
- wherein each element is packet in separated graduated dispensing devices.

The foregoing has outlined rather broadly the more pertinent and important features of the present invention in order that the detailed description of the invention that follows may be better understood, and so that the present contribution to the art can be more fully appreciated. Additional features of the invention that will be described hereinafter form the subject matter of the claims of the invention. It should be appreciated by those skilled in the art that the conception and the specific embodiments disclosed might be readily utilized as a basis for modifying or formulating other liquid formulations for carrying the same purposes of the present invention. It should also be realized by those skilled in the art that such equivalent formulations do not depart from the spirit and scope of the invention as set forth in the appended claims.

DETAILED DESCRIPTION OF THE INVENTION

The present invention concerns a pharmaceutical composition, including high concentrations of hormone that can be used by the compounding pharmacist safely, accurately, quickly, and inexpensively to produce individualized BHRT products such as ointments, creams, gels, or pastes.

The present invention concerns a concentrated hormone pharmaceutical composition comprising:
- at least one hormone;
- at least one solvent, and
- optionally a pharmaceutically acceptable carrier
- wherein the weight concentration of the at least one hormone in said composition is equal or greater than 0.6%.

In one of the embodiments, the concentrated is in a powdered form.

The term "pharmaceutically acceptable" means approved by a regulatory agency of the Federal or a state government or listed in the U.S. Pharmacopeia or other generally recognized pharmacopeia for use in animals, and more particularly in humans.

Hormones

The present invention contemplates the use of any one of the steroid hormones derived from cholesterol including, but not limited to, estrogen (estriol, estradiol, or estrone), progesterone, testosterone, dehydroepiandrosterone, norethisterone acetate, norgestrel, levonorgestrel gestodene CPA chlormadinone acetate, drospirorenone, and 3-ketodesogestrel.

The concentrates also could include, but not be limited to, an estriol concentrate, an estradiol concentrate, an estrone concentrate, a combination estriol, estradiol, and estrone (triest) concentrate in any proportion, preferably in a 8:1:1, 5:4:1, 6:3:1, or 7:2:1 ratio; a combination of estriol and estradiol concentrate (biest) in any proportion, preferably in a 5:5, 6:4, 7:3, 8:2, or 9:1 ratio; a combination estriol and estrone concentrate, a combination estradiol and estrone concentrate, a progesterone concentrate, a combination progesterone and estriol concentrate, a combination progesterone and estradiol concentrate, a combination progesterone and estrone concentrate, a combination progesterone and triest concentrate, a combination progesterone, estriol, and estradiol concentrate, a combination progesterone, estriol, and estrone concentrate, a combination progesterone estradiol, and estrone concentrate, any of the previously mentioned concentrates in combination with testosterone i.e. a combination triest, progesterone, and testosterone concentrate, a testosterone concentrate, any of the previously mentioned concentrates in combination with dehydroepiandrosterone (DHEA), and a DHEA concentrate.

In addition, any of the sex hormones may be used. Any androgen including, but not limited to, testosterone may be used. Any progestogen including, but not limited to, progesterone may be used. Any estrogen including, but not limited to, estriol, estradiol, or estrone may be used.

The concentrated composition of the present invention could include any concentration of any hormone or any combination of hormones in any proportion as long as the concentration is greater than the accepted physician prescribed concentrations to treat hormone deficiencies.

The present invention provides a concentrated pharmaceutical composition that contains any ratio of estriol to estradiol (biest) having between 6 mg/g and 900 mg/g of biest, preferably between 8 mg/g and 200 mg/g, even more preferably 10 mg/g to 60 mg/g.

In addition, the present invention provides a concentrated pharmaceutical composition that contains any ratio of estriol, estradiol, and estrone (triest) having between 6 mg/g and 900 mg/g of the triest, preferably between 8 mg/g and 200 mg/g, even more preferably 10 mg/g and 60 mg/g.

Furthermore, the present invention provides a concentrated pharmaceutical composition that contains between 10 mg/g and 900 mg/g of estriol, preferably between 15 mg/g and 300 mg/g, even more preferably 15 and 60 mg/g.

The present invention provides a concentrated pharmaceutical composition that contains between 1 mg/g and 900 mg/g of estradiol, preferably between 1.5 mg/g and 100 mg/g.

The present invention also provides a concentrated pharmaceutical composition that contains between 1 mg/g and 900 mg/g of estrone, preferably between 1.5 mg/g and 100 mg/g.

In addition, the present invention provides a concentrated pharmaceutical composition that contains between 10 mg/g and 800 mg/g of testosterone, preferably between 15 mg/g and 900 mg/g, even more preferably between 15 mg/g and 300 mg/g, for use in a female BHRT product.

Furthermore, the present invention provides a concentrated pharmaceutical compound that contains between 100 mg/g and 900 mg/g of testosterone, for use in a male BHRT product.

In addition, the present invention provides a concentrated pharmaceutical compound that contains between 200 mg/g and 900 mg/g of progesterone, more preferably between 400 mg/g and 800 mg/g, even more preferably 600 mg/g.

Furthermore, the present invention provides a concentrated pharmaceutical compound that contains between 10 mg/g and 900 mg/g of dehydroepiandrosterone or between 30 mg/g to 800 mg/g of pregnenolone.

The invention also concerns a concentrated hormone pharmaceutical composition comprising:
from about 0.6 to about 50% of at least one hormone;
from about 50 to about 90.4% of at least one solvent, and
optionally a pharmaceutically acceptable carrier
wherein the at least one hormone is chosen from estriol, estradiol, or combination thereof.

In addition, the invention concerns a concentrated hormone pharmaceutical composition comprising:
from about 0.6 to about 50% of at least one hormone;
from about 50 to about 90.4% of at least one solvent, and
optionally a pharmaceutically acceptable carrier
wherein the at least one hormone is chosen from estriol, estradiol, estrone, or combination thereof.

Furthermore, the invention concerns a concentrated hormone pharmaceutical composition comprising:
from about 0.8 to about 80% of at least one hormone;
from about 20 to about 90.2% of at least one solvent, and
optionally a pharmaceutically acceptable carrier
wherein the at least one hormone is testosterone.

The invention also concerns a concentrated hormone pharmaceutical composition comprising:
from about 8 to about 90% of at least one hormone;
from about 10 to about 92% of at least one solvent, and
optionally a pharmaceutically acceptable carrier
wherein the at least one hormone is progesterone.

Solvent (or Wetting agent)

The solvent or wetting agent can be any liquid that can dissolve, partially dissolve, wet, or suspend the hormone, or reduce the surface tension of a liquid to a value below the hormones critical surface tension.

In order for a solid to be incorporated into a liquid, the solids surface tension must be above the surface tension of the liquid. The best solvents produce a low air liquid surface tension, and are not readily adsorbed by the solid so as to produce nonwetting behavior.

The wetting agent or solvent acts by lowering the contact angle between the surface of the particle and the wetting liquid. Wetting agents replace a solid to air interface with a solid to liquid interface. The solvent or wetting agent should be miscible with the carrier.

The solvent or wetting agent could possibly be, but is not limited to, one or more of the following in any concentration: propylene glycol, ethoxy diglycol, glycerin, mineral oil, fixed oil, emu oil, peanut oil, vitamin E oil, acetone, amylene hydrate, benzyl benzoate, corn oil, cottonseed oil, diethylene glycol monoethyl ether, ethyl acetate, isopropyl alcohol, methyl alcohol, methylene chloride, methyl isobutyl ketone, polyethylene glycol 300, polyethylene glycol 400, polyethylene glycol 600, sesame oil, alcohol, a 50% ethoxy diglycol (diethylene glycol mono-ethyletherand) 50% propylene glycol mixture, water or mixtures threrof. Any combination of solvents may be employed.

The solvent or wetting agent should satisfy the following characteristics:
- the solvent or solvents should wet the hormone;
- the solvent should allow the hormone to be incorporated therein;
- the solvent or solvents should be compatible with the skin with the least possible number of adverse effects;
- the solvent or solvents should be smooth and pliable with no adverse odor;
- the solvent or solvents should have a color appealing to the consumer; and the solvent must be stable and must provide a stable vehicle for the medication.

The scope of the present invention is not limited by the solvents mentioned in the present application; any of those known in the pharmaceutical and cosmetic industries may be employed.

Pharmaceutically Acceptable Carrier

The carrier can be any suitable carrier that can be incorporated into a system, which can deliver bio-identical hormones transdermaly.

The formulations for the delivery of the pharmaceutical composition according to the present invention may be liquid, ointments, and creams.

The carrier can be chosen from ointment base, powder base, cream base, or a gel base.

Ointments are semisolid preparations, which are typically based on petrolatum or other petroleum derivatives. Creams containing the selected active agent, are, as known in the art, viscous liquid or semisolid emulsions, either oil-in-water or water-in-oil.

Cream bases are water-washable, and contain an oil phase, an emulsifier, and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant.

The specific ointment or cream base to be used, as will be appreciated by those skilled in the art, is one that will provide for optimum drug delivery. As with other carriers or vehicles, an ointment base should be inert, stable, nonirritating and non-sensitizing.

Powders may be formulated with the aid of any suitable powder base, such as talc, lactose, starch, and the like.

The pharmaceutical carrier could possibly be comprised of, but is not limited to, any or all of the following ingredients: an oil in water emulsion base, a water in oil emulsion base, an oleaginous base, an absorption base, a water soluble base an anhydrous gel, a pluronic F127/lecithin isopropyl palmitate gel, hydrous gel, purified water, white petrolatum, cetearyl alcohol, ceteareth-20, sorbitol solution, propylene glycol, simethicone, glyceryl monostearate, polyethylene glycol monostearate, sorbic acid, camellia sinensis (green tea) leaf extract, cholesterol, beeswax, cyclomethicone, C12-15 alkyl benzoate, plankton extract, acetyl ponta peptide-2, ocnethera biennis (evening primrose) root extract, dimethicone, hexyldecanol, dextran, stearyl alcohol, cetyl alcohol, pyrus malus (apple) fruit extract, acetyl hexapeptide-2, alnus firmirolia (yashabushi) extract, tocopheryl acetate (vitamin E acetate), glyceryl stearate, thioctic acid (a-lipoic acid), PEG-100 stearate, ascorbyl palmitate (vitamin C palmitate), tocopherol (vitamin E), tetrahexyldecyl ascorbate, sesamum indicum (sesame) seed oil, retinyl palmitate (vitamin A palmitate), prunus armeniaca (apricot) kernel oil, willow bark extract, phenoxyethanol, benzyl alcohol, potassium sorbate, glycerin, panthenol (pro-vitamin B5), retinal (vitamin A), lavandula agustifolia (lavender) oil, allantoin, polysorbate 20, xanthan gum, titanium dioxide, tetrasodium EDTA, topheryl linoleate (vitamin E linoleate), dimethylamino methylpropanol, ceramide 2, quaternium-15, polyacrylamide, magnesium aluminum silicate, laureth-7, citric acid, C13-14 isoparaffin, aloe barbadensis (aloe vera) leaf juice, cetearyl glucoside, 10-hydroxydecanoic acid, hydroxycaprylic acid, prunus amygdalus dulcis (sweet almond)oil, zinc PCA, zinc oxide, acacia, tragacanth, agar, pectin, gelatin, methyl cellulose, carboxymethylcellulose, carbomer, vitis vinifera (grape) seed extract, hibiscus sabdariffa flower extract, triticum vulgare (wheat)germ oil, citic acid, sodium hydroxymethylglycinate, isopropyl palmitate, squalane, cetearyl glucoside, lecithin, pluronic, cucumis sativus (cucumber) fruit extract, cetyl ricinoleate, caprylic/capric triglycerides, allantoin, ubiquinone (coenzyme Q10), helianthus annuus (hybrid sunflower) oil, cyclomethicone sodium PCA, stearic acid, glyceryl stearate, rose canina (rose hips) fruit oil, glycol, glycyrrhiza glabra (licorice) extract,aesculus hippacastanum (horse chestnut)extract, hydrolyzed yeast protein, calendula officinalis flower extract, centella asiatica (gotu kola) extract, ruscus aculeatus (butcher's broom)root extract, cyclopentasiloxane, evening primrose oil, PEG-75, PEG-150, sodium PCA, calendula officinalis flower extract, cyclopentasiloxane, hydrolyzed milk protein, ethoxy diglycol, lupinus albus seed oil, hydrophilic petrolatum, wool alcohol, sodium lauryl sulfate, PEG 4000, PEG 400, propylene glycol-ethanol, lecithin soya granular, sorbic acid, polyacrylamide, cytel alcohol, magnesium aluminum silicate, aloe vera (aloe barbadensis) prunus amygadalus amara (bitter almond) kenel oil, pro-lipo multi-emulsion liposomic system, propylparaben, methylparaben, imidazolidimyl urea, pluronic F127, alcohol, sodium hydroxide, DMAE, glycolic acid, edetate disodium dihydrate, urea, stearic acid, glyceryl monostearate, isopropyl myristate, polyoxyl 40 stearate, potassium sorbate, anhydrous ointment base, lanolin, anhydrous lanolin, emollient cream base, lanolin alcohol, mineral oil, glyceryl monostearate, stearic acid flakes, sualene, triethanolamine, krisgel 100, borago (borage) officinalis seed oil, simethicone, salicylic acid, dehydroacetic acid, benzyl alcohol, benzoic acid, benzethonium chloride, polysorbate 80, span, PEG-8 distearate/emerest 2712, hydrogenated vegetable oil, mineral oil (heavy), mineral oil (light), microethane FN 501, hydroxypropylcellulose, hydroxymethylcellulose, methylcellulose, avicel, polyglygol 300, polyglycol 8000, paraffin waxes, propylene glycol isostearate, isostearyl alcohol, white ointment USP, yellow ointment NF, oleic acid USP, olive oil USP, paraffin USP, petrolatum NF, spermaceti wax USP, synthetic spermaceti NF, starch glycerite NF, white wax USP, yellow wax USP, dbutylated hydroxy toluene, or combination thereof.

The carrier should satisfy the following characteristics:
- the base should allow the wetted hormone to be incorporated therein;
- the base should be compatible with the skin with the least possible number of adverse effects;
- the base should be smooth and pliable with no adverse odor;
- the base should have a color appealing to the consumer;
- the base must be stable and must provide a stable vehicle for the medication; and
- the base should be able to readily release the medication incorporated therein into the skin.

Additional Ingredients

The concentrated pharmaceutical composition according to the invention optionally can include antioxidants to prevent oxidation of any of the components therein. The antioxidant may include, but are not limited to, ascorbic acid, sodium ascorbate, sodium formaldehyde sulfoxylate, sodium bisulfite, sodium nitrite, sodium thiosulfate, sodium metabisulfite, sodium sulfite, sulfur dioxide, tannic acid, thioglycerol, tert-butyl-hydroquinone, thioglycolic acid, thiolactic acid, thiosorbitol, thiourea, tocopherols, butylated hydroxy toluene, acetone sodium sulfate, acetylcysteine, lipoic acid (sodium salt), tocopherol, ascorbyl palmitate, butylated hydroxyanisole, calcium ascorbate, calcium bisulfite, calcium sulfite, cysteine, dilauryl thiodipropionate, dithiothreitol, dodecyl gallate, ethoxyquin, ethyl gallate, gallic acid, glutathione, gossypol, hydroquinone, 4-hydroxymethyl-2,6-di-tert-butylphenol, hypophosphorus acid, isoascorbic acid, lecithin, monothioglycerol, B-naphthol, nordihydroguaiaretic acid, octyl gallate, potassium metabisulfite, propyl gallate, sesamol, or Vitamin E. These antioxidants are not particularly limited; any of those known in the pharmaceutical or cosmetic industries may be used.

In addition, the concentrated pharmaceutical composition according to the invention optionally may include preservatives to prevent the growth of bacteria or fungi in the final product. These may include, but are not limited to, thimerosal, benzyl alcohol, imidazolidinyl urea, quaternium-15, benzalkonium chloride, chlohexidine, chlorbutanol, phenol, cresol, chlorothymol, chloroxylenol, P-chlorometaxylenol, sodium benzoate, potassium sorbate, boric acid, methyl paraben, propylparaben, sorbic acid, alcohol, benzethonium chloride, benzoic acids and salts, benzyl alcohol, sodium benzoate, boric acids and salts, cetylpyridinium chloride, cetyltrimethyl ammonium bromide, chlorbutanol, clorocresol, imidazolidinyl urea, metacresol, myristylgamma picolinium chloride, nitromersol, parabens(benzyl, butyl, methyl, propyl), phenol, phenyl phenol, phenylethyl alcohol, phenylmercuric acetate/nitrate, sorbic acids and salts, thimerosal, hydroxybezoate esters and phenyl ethyl alcohol. These preservatives are not particularly limited; any of those known in the pharmaceutical or cosmetic industries may be used.

Further, the concentrated composition of the invention optionally can include chelating agents and synergists added, which may include, but are not limited to, EDTA and salts, alkyl gallates, ascorbic acid, boric acid, citraconic acid, gluconic acid, hydroxyquinolone sulfate, maleic acid, phosphoric acid, polysorbates, saccharic acid, tartaric acid, tryptophan and citric acid. These chelating agents and synergists are not particularly limited; any of those known in the pharmaceutical or cosmetic industries may be used.

Further, the concentrated composition of the invention optionally can include emulsifying agents to facilitate the formation of an emulsion. The emulsifying agents may include, but are not limited to acacia, tragacanth, agar, pectin, gelatin, methyl cellulose, carboxymethylcellulose, PEG-40 castor oil, PEG 300, polysorbate 20, polysorbate 40, polysorbate 80, sorbitan monopalmitate, simethicone, or any synthetic anionic, cationic, or nonionic emulsifying agents. These emulsifying agents are not particularly limited; any of those known in the pharmaceutical or cosmetic industries may be used.

Further, the concentrated composition of the invention optionally can include suspending agents to increase viscosity. The suspending agents may include, but are not limited to, acasia, bentonite, carboxymethylcellulose, methycellulose, hydroxypropylcellulose, carbomer resins, colloidal silicon dioxide, sodium alginate, tragacanth, agar, alginic acid, attapulgite, bentonite, carrageenan, cellulose, microcrystalline cellulose, microcrystalline carboxymethylcellulose, dextrin, gelatin, guar gum, hydroxyethylcellulose, hydroxypropylmethyl-cellulose, magnesium aluminum silicate, pectin, polaxamer, polyethylene oxide, polyvinyl alcohol, povidone, propylene glycol alginate, xanthan gum, and veegum. These suspending agents are not particularly limited; any of those known in the pharmaceutical or cosmetic industries may be used.

Further, the concentrated composition of the present invention optionally can include stiffening agents to increase viscosity. The stiffening agents may include, but are not limited to, hydrogenated castor oil, cetostearyl alcohol, cetyl alcohol, cetyl esters wax, hard fat, paraffin, synthetic paraffin, stearyl alcohol, emulsifying wax, white wax, and yellow wax. These stiffening agents are not particularly limited; any of those known in the pharmaceutical or cosmetic industries may be used.

Further, the concentrated composition of the present invention optionally can include any substance, which can increase or decrease the pH of the system added. The pH modifiers can be either acidifying agents or alkalizing agents. The pH can be modified to any pH, which is deemed suitable.

These pH modifiers may include but are not limited to, (acidifying agents) acetic acid, acetic acid glacial USP, citric acid, hydrochloric acid, fumaric acid, lactic acid, nitric acid, phosphoric acid, sodium phosphate monobasic, sulfuric acid, malic acid, tartaric acid propionic acid, (alkalizing agents) ammonia solution, ammonium carbonate, diethanolamine, monoethanolamine, sodium bicarbonate, sodium borate, sodium phosphate dibasic, trolamine, potassium hydroxide, sodium hydroxide, and sodium carbonate. These PH modifiers are not particularly limited; any of those known in the pharmaceutical or cosmetic industries may be used.

Further, the concentrated composition of the present invention optionally can include any solubilizing agent. These agents may include but are not limited to, benzalkonium chloride, cetylpyridium chloride, benzethonium chloride, docusate sodium, nonoxynol 9, octoxynol 9, polaxamer(s), polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, and tyloxapol. These wetting and/or solubilizing agents are not particularly limited; any of those known in the pharmaceutical or cosmetic industries may be used.

Further, the concentrated composition of the present invention optionally can include any substance, which can increase the shelf life of said product. These agents may include but are not limited to, vitamin E and ascorbic acid. These substances are not particularly limited; any of those known in the pharmaceutical or cosmetic industries may be used.

In one embodiment, the concentrated hormone pharmaceutical composition contains 32 mg/g estriol, 4 mg/g estradiol, and 4 mg/g estrone concentrates (triest) in 960 mg/g of a mixture of 50% ethoxy diglycol/50% propylene glycol. The estriol, estradiol, and estrone are present in the composition at 8:1:1, 6:3:1, 5:4:1 or 7:2:1 ratios.

After extensive research, the present inventor discovered that the combination of ethoxy diglycol and propylene glycol in any ratio has the ability to dissolve the combination of estriol, estradiol, and estrone (triest) in any ratio or testosterone alone better than using any of the solvents alone.

In another embodiment, the concentrated hormone pharmaceutical composition contains 32 mg/g estriol and 8 mg/g estradiol concentrates (biest) in 960 mg/g of a mixture of 50% ethoxy diglycol/50% propylene glycol. The estriol and estradiol are present in the composition at 8:2, 5:5, 6:4, 7:3, or 9:1 ratio.

In another embodiment, the concentrated hormone pharmaceutical composition contains 64 mg/g testosterone concentrate in a mixture of 50% ethoxy diglycol/50% propylene glycol for women and 150 mg/g of a mixture of 50% ethoxy diglycol/50% propylene glycol for men.

In another embodiment, the concentrated hormone pharmaceutical composition contains 600 mg/g of progesterone concentrate in vanishing cream type oil in water emulsion base.

In another embodiment, the concentrated hormone pharmaceutical composition contains 0.8 g/g estriol, 0.1 g/g estradiol, and 0.1 g/g estrone (triest) in a powdered form optionally mixed with any amount of a filler or in the following ratios: 8:1:1, 7:2:1, 6:3:1, or 5:4:1.

In another preferred embodiment, the concentrated hormone pharmaceutical composition contains 0.8 g/g estriol and 0.2 g/g estradiol (biest) in a powdered form optionally mixed with any amount of a filler or in the following ratios: 5:5, 6:4, 7:3, 8:2, or 9:1.

In another preferred embodiment, the concentrated hormone pharmaceutical composition comprises:
- at least one hormone;
- optionally a powdered base;
- wherein the at least one hormone is chosen from estriol, estradiol, or combination thereof; and
- wherein the composition is in a powdered form.

The at least one hormone a combination of estriol, estradiol in a ratio of 5:5, 6:4, 7:3, 8:2, or 9:1.

In another preferred embodiment, the concentrated hormone pharmaceutical composition comprising:
- at least one hormone; and
- optionally a powdered base;
- wherein the at least one hormone is chosen from estriol, estradiol, estrone, or combination thereof; and
- wherein the composition is in a powdered form.

The at least one hormone is a combination of estriol, estradiol, and estrone in a ratio of 5:4:1, 6:3:1, 7:2:1, or 8:1:1.

Examples of powdered bases suitable for use in the pharmaceutical compositions disclosed herein include, but are not limited to, talc, calcium carbonate, microcrystalline cellulose, powdered cellulose, dextrates, kaolin, rice, flour, chalk, silica gel, sodium stearate, glycerol monostearate, mannitol, silicic acid, sorbitol, starch, pre-gelatinized starch, and mixtures thereof.

In another embodiment of the present invention, the at least one hormone is combined directly with the pharmaceutically acceptable carrier (ointment, cream, powder or gel base) without the prior use of a solvent or solvents.

In a further embodiment of the present invention, the hormone is weighed and packaged unadulterated in an appropriate container. The solvent or solvents and/or optionally the ointment, cream, gel base, or powdered base are packaged in a separate container. The two products are sold together as a kit. The two components are to be combined by whoever purchases the kit to formulate the hormone concentrate system.

Color Coded-concentrated Pharmaceutical Composition

The present invention also provides a color-coded concentrated hormone composition to help the pharmacist quickly choose the composition to be used.

The advantage of having color-coded concentrates are as follows:

helps to rapidly identify the concentrate.

ensures that all concentrates required to be contained in a final product are present in said final product. This is made possible because each combination and permutation of the concentrates will result in a distinct color profile. If the final product does not match the color profile for that medication, you know you have done something wrong; and ensures complete mixing of the final product. When the final product is a uniform color throughout, adequate mixing will have taken place.

The coloring agent could possibly be, but is not limited to one of the following: acid red 52, basic fuchsin USP, brilliant green, caramel NF, carmine NO.40, congo red, D&C green NO.5, D&C green NO.6, D&C green NO. 8, D&C orange NO.4, D&C red NO.4, D&C red NO.6, D&C red NO.17, D&C red NO. 22, D&C red NO.28, D&C red NO.33, D&C .violet NO.2, D&C yellow NO.8, D&C yellow NO.10, D&C yellow NO.11, F.D. &C. blue NO.1, F.D. &C. blue NO.2, F.D. &C. green NO.3, F.D. &C. red NO.3, F.D. &C. red NO.19, F.D. &C. red NO.40, F.D. &C. yellow NO.5, F.D. &C. yellow NO.6, malachite green oxalate, rose Bengal, saffron, scarlet red, and any food color in liquid or powder form. The coloring agent is not particularly limited; any of those known in the pharmaceutical or cosmetic industries may be employed. Preferably, the coloring agent will not noticeably color the skin. It should be compatible with the skin with the least number of adverse effects.

The concentrates according to the present invention would be manufactured using extensive safety measures. These include, but are not limited to, the use of custom built clean rooms (a room designed specifically for compounding with hazardous materials), high velocity air flow units fitted with high emission particulate air (HEPA) filters, custom built ventilation systems, protective suits, protective eyewear, protective gloves, and protective HEPA filter masks.

A pharmacist or technician trained in the art of compounding BHRT ointments, creams, gels, and pastes will manufacture these concentrates.

An advantage of the present invention is the composition contains a high concentration of hormones (higher than the prescribed levels), thus the pharmacist can easily use the concentrates to produce a custom tailored BHRT product without risking his own health.

The present invention also contemplates a method for producing the concentrated composition of the present invention. The method comprises the steps of:
- measuring at least one hormone, a solvent and/or optionally a carrier by using an electronic balance in a clean room;
- combining the ingredients of step a by using an industrial scale mixer to ensure thorough mixing; and
- running the mixture of step b through a large-scale ointment mill or homogenizer to decrease the particle size of the drug, and
- optionally, heating the concentrate to facilitate the formation of a solution,
- wherein the hormone concentration is from about 0.6 to about 80%.

The concentrated hormone pharmaceutical composition of the present invention may be further divided with similar or different carrier materials to concentrations that are suitable for practical use by the compounding pharmacist.

If the medication is not thoroughly mixed, then it will not contain a uniform concentration of the drug throughout. A solution will provide the best distribution of drug throughout the system.

Running the mixture through a large-scale ointment mill or using a homogenizer decreases the particle size and increases the absorbability, because smaller drug particles will more readily penetrate the dermis. This process also ensures a non-gritty, pharmaceutically elegant, and cosmetically pleasing final product.

The present invention is also in combination with a dispensing device to provide a means to measure and combine, quickly and accurately, quantities of hormones with appropriate ointment, cream, or gel bases while minimizing exposure to hazardous airborne hormone particles. Thus, airborne particles are drastically reduced because the hormones are incorporated into a liquid or semi-solid form.

EXAMPLE 1

The formulation was made in the following manner (total quantity: 120 ml and a concentration of 300 mg/g of testosterone)
36g of testosterone were weighed out.
b) the volume was brought up to 120 ml with approximately 84 ml of an anhydrous gel base.
1 drop of blue food coloring was added.
the mixture was combined in an electronic mortar and pestle.
the mixture was run through an ointment mill to decrease the particle size of the testosterone.
the mixture was transferred into 4 30 ml luer lock syringes.
This is what the mixture is sold in.

EXAMPLE 2

The formulation, according to the invention, was made in the following manner (total quantity: 1000 ml and a concentration of 62.5 mg/g of triest (estriol, estradiol, and estrone in an 8:1:1 ratio)
50 g of estriol were weighed out and wetted with 50 ml of ethoxy diglycol.
6.25 g of estradiol were weighed out and wetted with 6.25 ml of ethoxy diglycol.
6.25 g of estrone were weighed out and wetted with 6.25 ml of ethoxy diglycol.
10 drops of red food coloring was added.
the volume was brought up to 1000 ml with approximately 875 ml of oil in water emulsion type vanishing cream base.
the mixture was combined in an industrial mixer.
the mixture was run through an ointment mill to decrease the particle size of the estrogens.
the mixture was transferred into 33 30 ml luer lock syringes.
This is what the mixture is sold in.

EXAMPLE 3

The formulation, according to the invention, was made in the following manner (total quantity: 5000 ml and a concentration of 400 mg/g of progesterone)
2000 g of progesterone were weighed out.
the progesterone was combined with an oil phase, an aqueous phase and an emulsifier to formulate a water in oil emulsion type cream base with a final volume (including the progesterone) of 5000 ml.
50 drops of yellow food coloring was added.
the mixture was combined in an industrial mixer.
the mixture was run through an ointment mill to decrease the particle size of the progesterone.
the mixture was transferred into 83 60 ml luer lock syringes.
This is what the mixture is sold in.

EXAMPLE 4

The formulation, according to the invention, was made in the following manner (total quantity: 10000 ml and a concentration of 600 mg/g of progesterone (this is a paste)
6000 g of progesterone were weighed out.
the progesterone was combined with 2000 ml of ethoxy diglycol.
100 drops of yellow food coloring was added.
an oil in water emulsion type vanishing cream base was used to bring the final volume to 10000 ml, approximately 2900 g of the cream.
the mixture was combined in an industrial mixer.
the mixture was run through an ointment mill to decrease the particle size of the progesterone.
the mixture was transferred into 50 ml ointment jar. This is what the mixture is sold in.

EXAMPLE 5

The formulation, according to the invention, was made in the following manner (total quantity: 2000 ml and a concentration of 300 mg/g of testosterone)
600 g of testosterone were weighed out.
The testosterone was combined with approximately 400 ml of ethoxy diglycol.
15 drops of blue food coloring was added.
Approximately 1000 ml of a 1% hydroxypropylcellulose in ethoxy diglycol anhydrous gel was added to bring the final volume to 2000 ml.
The mixture was combined in an industrial mixer.
The mixture was further mixed with a homogenizer to decrease the particle size of the testosterone.
The mixture was transferred to 40 50 ml bottles fitted with adapter caps. A 5 ml oral syringe and a 1 ml oral syringe, fitting the adapter cap, were packaged with each bottle to be used as measuring devices.

EXAMPLE 6

The formulation, according to the invention, was made in the following manner (total quantity: 10000 ml and a concentration of 40 mg/g of triest (estriol, estradiol, and estrone in an 8:1:1 ratio))
320 g of estriol were weighed out.
40 g of estradiol were weighed out.
40 g of estrone were weighed out.
100 drops of red food coloring was added.
The volume was brought up to 10000 ml with a 50% ethoxy diglycol and 50% propylene glycol combination.
The mixture was combined in an industrial mixer.
The mixture was heated to 60 degrees Celsius for 2 hours in order to facilitate solution of the triest powder.
The solution was transferred into 100 100 ml bottles fitted with adapter caps, accompanied with 1 ml, 5 ml, and 10 ml oral syringes. This is what the mixture is sold in.

EXAMPLE 7

The formulation, according to the invention, was made in the following manner (total quantity: 2000 ml and a concentration of 70mg/g of testosterone)

140 g of testosterone were weighed out.

15 drops of blue food coloring was added.

The testosterone was combined with approximately 1860 ml of ethoxy diglycol, enough to bring the final volume to 2000 ml.

The mixture was combined in an industrial mixer.

The mixture will now be a solution.

The solution was transferred to 40 50 ml bottles fitted with adapter caps. A 5 ml oral syringe and a 1 ml oral syringe, fitting the adapter cap, were packaged with each bottle to be used as measuring devices.

EXAMPLE 8

The formulation, according to the invention, was made in the following manner (total quantity: 2000 ml and a concentration of 150 mg/g of testosterone)

300 g of testosterone were weighed out.

15 drops of blue food coloring was added.

The testosterone was combined with approximately 1700 ml of a 50% ethoxy diglycol and 50% propylene glycol mixture, enough to bring the final volume to 2000 ml.

The mixture was heated to 60 degrees Celsius and mixed in an industrial mixer.

The mixture will now be a solution.

The solution was transferred to 40 50 ml bottles fitted with adapter caps. A 5 ml oral syringe and a 1 ml oral syringe, fitting the adapter cap, were packaged with each bottle to be used as measuring devices.

EXAMPLE 9

The formulation, according to the invention, was made in the following manner (total quantity: 1000 gm and a concentration of 62.5 mg/gm of triest (estriol, estradiol, and estrone in an 8:1:1 ratio))

50 g of estriol were weighed.

6.25 g of estradiol were weighed out.

6.25 g of estrone were weighed out.

The weight was brought up to 1000 gm with approximately 937.5 gm of lactose.

The mixture was combined in an industrial mixer.

The mixture was transferred to 10 100 gm jars.

EXAMPLE 10

The formulation, according to the invention, was made in the following manner (total quantity: 1000 ml and a concentration of 40 mg/g of triest (estriol, estradiol, and estrone in an 8:1:1 ratio))

32 g of estriol were weighed out.

4 g of estradiol were weighed out.

4 g of estrone were weighed out.

The three powders were combined.

4 g of this combination were transferred into each of 10 100 ml bottles fitted with adapter caps.

Approximately 96 ml, enough to bring the final volume to 100 ml, of a 50% ethoxy diglycol and 50% propylene glycol mixture was transferred to each of 10 other 100 ml bottles fitted with adapter caps.

The bottles could be sold as a kit or as 2 separate entities. 1 bottle of powder and 1 bottle of solvent would constitute 1 kit. The purchaser would add the solvent to the bottle containing the powder using an oral syringe so as not to be exposed to the powdered hormones. With stirring, at 50 degrees Celsius, the combination would form a solution. This solution is the hormone concentrate.

EXAMPLE 11

The formulation, according to the invention, was made in the following manner (total quantity: 100 ml and a concentration of 40 mg/g of triest (estriol, estradiol, and estrone in an 8:1:1 ratio))

3.2 g of estriol were weighed out and transferred into a 100 ml bottle.

0.4 g of estradiol were weighed out and transferred into a 100 ml bottle.

0.4 g of estrone were weighed out and transferred into a 100 ml bottle.

Enough colored 50% propylene glycol/50% ethoxy diglycol mixture to combine with the estriol, estradiol, and estrone to bring the final volume to 100 ml, approximately 96 ml, was measured and transferred into a 100 ml bottle.

EXAMPLE 12

The formulation, according to the invention, was made in the following manner (total quantity: 120 ml and a concentration of 300 mg/g of testosterone)

36 g of testosterone were weighed out.

The volume was brought up to 120 ml with approximately 84 ml of a glycerin.

1 drop of blue food coloring was added.

The mixture was combined in an electronic mortar and pestle.

The mixture was run through an ointment mill to decrease the particle size of the testosterone.

The mixture was transferred into 4 30 ml luer lock syringes.

This is what the mixture is sold in.

The mixture of example 11 will be sold as a kit in which the pharmacist will combine the elements to produce the hormone concentrate system. The pharmacist will transfer the liquid into the bottle containing the estriol, then transfer this mixture into the bottle containing the estradiol, then transfer this mixture into the bottle containing the estrone. This final solution will be the triest concentrate.

These concentrates could be packaged in, or with, any graduated dispensing device that lends itself to accurately measure specific volumes of liquids or semi-solids including, but not limited to, a metered dose tube, a metered dose pump, a metered dose syringe, a bottle, an ointment jar, a metered dose spray bottle, a bottle fitted with an adapter cap, and a luer lock syringe, a pipette, a bottle top dispenser, a burette, and a metered dose scoop. The packaging, dispensing, or measuring devices are not particularly limited. Any of those known in the pharmaceutical, chemical, or cosmetic industries may be used.

A specific amount, different for each compound, of these concentrates would be combined with an appropriate amount of any ointment, cream, or gel base, suitable for transdermal administration of bio-identical hormones, to form a final product which contains the doctor prescribed concentration of each bio-identical hormone.

The pharmacist using the concentrate, according to the invention, can easily incorporate the hormone into the compounding BHRT ointments, creams, gels, or pastes by:

Putting on protective gloves.

Calculating the total amount of hormones needed to compound a medication of a specific volume and concentration depending on the patient necessities;

Determining how many milliliters of the appropriate concentrate will contain the total amount of hormone needed for the compound.

Measuring the volume of concentrate containing the total amount of hormone needed. This is done using an appropriate liquid or semi-solid measurement system.

Repeating steps 2 through 4 for each hormone to be present in the final preparation.

Calculating the amount of the appropriate ointment, cream, or gel base, which is needed for the final product. This is accomplished by subtracting the total volume of concentrates used from the total volume needed.

Combining the ointment, cream, or gel base and the concentrates on a glass ointment slab, using an EMP, mixing them an appropriate number of times between two luer lock syringes attached together using a luer lock to luer lock adapter or any other form of mixing. When the color is uniform throughout, adequate mixing has taken place.

In another embodiment, the pharmaceutically acceptable carrier is sold inside a metered dose device. These will make unnecessary to use a scale in measuring and making BHRT creams. This is a distinct advantage for pharmacies not presently engaged in the art of compounding. The only additional equipment needed is a spatula for mixing. If the carrier is not packaged in a metered device, then the cream would have to be weighed and measured using a scale, which takes more time as well as additional cost to purchase the scale.

In addition, the invention concerns a kit for producing a concentrated hormone pharmaceutical composition, the kit comprising:

at least one hormone;

at least one solvent, and optionally a pharmaceutically acceptable carrier, wherein each element is packet in separated graduated dispensing devices.

In a further embodiment, the kit of the present invention comprises separately packing the at least one hormone and the at least one solvent in a container having internal divisions, wherein the at least one hormone and the at least one solvent are combined by the purchaser to form the hormone concentrate system.

Advantages

The concentrated composition of the invention offers numerous advantages over compounding BHRT ointments, creams, gels, or pastes using a traditional method with commercially available hormones in powder form.

Using these concentrates, combined with an appropriate liquid or semi-solid measurement system, in the place of powdered hormones and a scale, will dramatically reduce the risk of exposure to hazardous airborne hormone particles. This is due to the fact that the powdered hormones are incorporated into a liquid or semi-solid. This means that the need for inconvenient, expensive, and time-consuming safety measures is greatly reduced. Since there are relatively few airborne particles, there is little or no need for the use of custom built clean rooms (a room designed specifically for compounding with hazardous materials), high velocity air flow units fitted with HEPA filters, custom built ventilation systems, protective suits, protective eyewear, or protective HEPA filter masks. The only safety measure definitely required is protective gloves.

When the concentrates are manufactured, they are mixed using an industrial mixer, which ensures thorough mixing. This alleviates the need for purchasing and using an EMP for compounding BHRT ointments, creams, gels, or pastes. They are also run through a large ointment mill or homogenizer to reduce the particle size of the drug. This will increase absorbability, as smaller drug particles will more readily penetrate the dermis. This process also ensures a non-gritty, pharmaceutically elegant, and cosmetically pleasing product. This alleviates the need for purchasing and using an ointment mill for compounding BHRT ointments, creams, gels, or pastes.

The concentrates of the present invention offer the advantage that they are easier and most accurate to measure. The fact that the hormones are in solution results in a superior final product, the product produced from the concentrates and dispensed to the patient. This is due to the fact that there are no particles. All particles have been solubilized. This results in a pharmaceutically elegant and easily penetrateable final product.

The fact that the concentrates are color-coded will greatly reduce the chance of compounding errors. The color system should reduce the inadvertent use of one hormone concentrate instead of another. It will also ensure that all of the intended concentrates are present in the final product. This is accomplished because each combination and permutation of the concentrates will have a distinct color profile. If the final product does not match its profile, then you know something has been done incorrectly. The color system will also help ensure that the final product is uniformly mixed. When the final product is a consistent color throughout, you will have adequate mixing. At the present time, most compounding pharmacists do not have an adequate system in place to ensure proper mixing. Without proper mixing, the final product will not have a uniform concentration of the hormones throughout the system.

Since the concentrate system alleviates the need for most of the safety measures required for compounding these medications, as well as the need for a scale, EMP, and ointment mill, it significantly reduces the cost of compounding these medications. The concentrate system also significantly decreases the time needed to compound them. This is because the number of steps needed to compound them is drastically reduced. This increase in efficiency will result in a proportional decrease in labor costs.

The hormone concentrates and an appropriate liquid or semi-solid measurement system will make it possible for any pharmacist in any setting to safely and accurately compound BHRT ointments, creams, gels, and pastes. At the present time, only compounding pharmacists with elaborate compounding facilities and the proper equipment can compound them safely and accurately. Using this invention, any pharmacist in any setting will now be able to safely, quickly, inexpensively, and accurately compound BHRT ointments, creams, gels, and pastes. This will inevitably result in an increase in the availability of these medications to the public.

The fact that each final product, the product dispensed to the patient, has a distinct colour profile has an additional benefit. It will help decrease the chance of dispensing the wrong product to a patient. If a patient was to receive a Tri-est cream (which should be pink) but a blue cream was labeled Tri-Est, the pharmacist would be easily able to identify the error. Also, the patient would be able to tell that their previous cream was pink and this one is blue, bringing this to the pharmacist's attention. At present time all hormone creams are white, making it all but impossible to detect a labeling error. The colour coding also decreases the likely hood of choosing the wrong cream from the stock as each cream is readily identifiable. The coloring system allows each final product to be differentiated from one another.

What is claimed is:

1. A concentrated liquid hormone composition for use in compounding a pharmaceutical product for topically delivering one or more steroid hormones to a subject in need of hormone replacement therapy, comprising one or more naturally occurring steroid hormone(s) dissolved in a solvent mixture consisting of ethoxy diglycol and propylene glycol.

2. The concentrated liquid hormone composition of claim 1, wherein the solvent mixture is about 50% ethoxy diglycol and about 50% propylene glycol (vol/vol).

3. The concentrated liquid hormone composition of claim 1, comprising one or more estrogen(s) at a total concentration of at least 40 mg per gram.

4. The concentrated liquid hormone composition of claim 3, wherein said estrogen(s) are selected from estriol, estradiol, and estrone.

5. The concentrated liquid hormone composition of claim 1, comprising at least one androgen at a concentration of at least 150 mg per gram.

6. The concentrated liquid hormone composition of claim 5, wherein said androgen is selected from testosterone and dehydroepiandrosterone (DHEA).

7. The concentrated liquid hormone composition of claim 1, comprising at least one progestagen at a concentration of at least 200 mg per gram.

8. The concentrated liquid hormone composition of claim 7, wherein said progestagen is selected from progesterone and pregnenolone.

9. A concentrated liquid hormone composition for use in compounding a pharmaceutical product for delivering hormones to a subject in need of hormone replacement therapy, comprising a plurality of different naturally occurring estrogens dissolved in a solvent mixture of ethoxy diglycol and propylene glycol at a total concentration of at least 6 mg of estrogens per gram.

10. The concentrated composition of claim 9, wherein the composition comprises about 40 mg of estrogens per gram.

11. The concentrated composition of claim 9, wherein the estrogens are estriol, estradiol, and estrone.

12. The concentrated composition of claim 11, wherein the ratio of estriol, estradiol, and estrone by weight is 8:1:1, 5:4:1, 6:3:1, or 7:2:1.

13. A method for preparing the concentrated composition of any of claims 1, 2 to 9, 10 ,11, and 12, comprising:
   a) combining said steroid hormone(s) with said solvent(s); and
   b) processing said combination in an ointment mill or homogenizer to decrease particle size of said hormone(s) in the combination.

14. A plurality of concentrated hormone compositions according to any of claims 1, 2 to 9, 10 ,11, and 12.

15. A method for compounding a pharmaceutical product for administering one or more hormones to a consumer in need of hormone replacement therapy, whereby the product is custom tailored for each individual consumer, the method comprising:
   a) obtaining a plurality of concentrated liquid reagent compositions, at least one of which comprises one or more steroid hormone(s) dissolved in ethoxy diglycol and propylene glycol;
   b) ascertaining the needs of an individual consumer; and
   c) compounding a plurality of said concentrated reagent composition(s) into said pharmaceutical product at a ratio that is custom tailored to the individual needs of said consumer, wherein the final concentration of each of said steroid hormone(s) in the pharmaceutical product is sufficient to be therapeutically effective for the consumer in accordance with their needs.

16. The compounding method of claim 15, wherein the needs of the consumer is ascertained by way of a prescription from a doctor for replacement of particular hormone(s) each in a particular amount.

17. The compounding method of claim 15, wherein at least one of the concentrated reagent compositions contains one or more estrogen(s) dissolved at a total concentration of at least 40 mg per gram.

18. The compounding method of claim 17, wherein said estrogen(s) are selected from estriol, estradiol, and estrone.

19. The compounding method of claim 15, wherein at least one of the concentrated reagent compositions contains at least one androgen at a concentration of at least 150 mg per gram.

20. The compounding method of claim 19, wherein said androgen is selected from testosterone and dehydroepiandrosterone (DHEA).

21. The compounding method of claim 15, wherein at least one of the concentrated reagent compositions contains at least one progestagen at a concentration of at least 200 mg per gram.

22. The compounding method of claim 21, wherein said progestagen is selected from progesterone and pregnenolone.

23. The compounding method of claim 15, comprising combining a plurality of concentrated reagent compositions, each containing a different estrogen.

24. The compounding method of claim 15, whereby the pharmaceutical product produced contains estriol and estradiol.

25. The compounding method of claim 24, wherein the ratio of estriol:estradiol by weight in the final product is 5:5, 6:4, 7:3, 8:2, or 9:1.

26. The compounding method of claim 15, whereby the pharmaceutical product produced contains estriol, estradiol, and estrone.

27. The compounding method of claim 26, wherein the ratio of estriol, estradiol, and estrone by weight in the final product is 8:1:1, 5:4:1, 6:3:1, or 7:2:1.

28. The compounding method of claim 15, in which one or more of said concentrated reagent composition(s) is color coded, and the method further comprises verifying the identity of the hormone(s) in the product according to the color of the pharmaceutical product after compounding.

29. The compounding method of claim 15, in which one or more of said concentrated reagent composition(s) is color coded, and the method further comprises verifying that the ingredients of the product have been adequately mixed according to whether the final product is a uniform color throughout.

* * * * *